United States Patent [19]
Chaudhari et al.

[11] Patent Number: 5,792,875
[45] Date of Patent: Aug. 11, 1998

[54] CATALYTIC PRODUCTION OF BUTYROLACTONE OR TETRAHYDROFURAN

[75] Inventors: Raghunath Vitthal Chaudhari; Subhash Hari Vaidya, both of Maharashtra, India

[73] Assignee: Council of Scientific & Industrial Research, New Delhi, India

[21] Appl. No.: 658,250

[22] Filed: Jun. 4, 1996

Related U.S. Application Data

[62] Division of Ser. No. 219,493, Mar. 29, 1994, abandoned.

[51] Int. Cl.$^6$ .................... C07D 307/58; C07D 307/08
[52] U.S. Cl. ............................. 549/326; 549/508
[58] Field of Search ................... 549/326, 508

[56] References Cited

U.S. PATENT DOCUMENTS

| | | | |
|---|---|---|---|
| 3,781,251 | 12/1973 | Kominami et al. | 252/432 |
| 3,869,521 | 3/1975 | Benson | 260/667 |
| 5,118,884 | 6/1992 | Didillon et al. | 568/875 |
| 5,502,217 | 3/1996 | Fuchikami et al. | 549/326 |

FOREIGN PATENT DOCUMENTS

| | | |
|---|---|---|
| 724908 | 8/1996 | European Pat. Off. |
| 165540 | 7/1988 | India |

OTHER PUBLICATIONS

"Catalysis" Kirk–Othmer, ed., *Concise Encyclopedia of Chemical Technology*, pp. 224–225.

Deshpande, et al., "Studies on Ruthenium–Tin Boride Catalysts I Characterization" *Journal of Catalysis*, 121, 165–173 (1990).

Dashpande, et al., "Studies on Ruthenium–Tin Boride Catalysts. II Hydrogenation of Fatty Acid Esters to Fatty Alcohols" *Journal of Catalysis*, 121, 174–182 (1990).

*Primary Examiner*—Bernard Dentz
*Attorney, Agent, or Firm*—Ladas & Parry

[57] ABSTRACT

A process for the preparation of supported bimetallic catalyst useful for the hydrogenation of esters of dicarboxylic acids, which comprises impregnating activated alumina powder with transition metal by contacting the said solid alumina powder with an aqueous solution of a salt of a transition metal, treating the said transition metal salt impregnated alumina powder with an aqueous solution of a salt of group (IV) metal in acidic medium so as to have ratio of transition metal to group (IV) A metal in the range of 1:5 to 1:20, further treating the bimetallic impregnated alumina powder with an alkali solution followed by a solution of boron containing compound, finally washing and drying the resultant supported catalyst.

8 Claims, No Drawings

CATALYTIC PRODUCTION OF BUTYROLACTONE OR TETRAHYDROFURAN

This is a divisional of application Ser. No. 08/219,493 filed on Mar. 29, 1994 now abandoned.

BACKGROUND OF THE INVENTION

1. Field of the Invention

This invention relates to a process for the preparation of supported bimetallic catalysts and a process for selective hydrogenation of dicarboxylic acid esters.

The present invention specifically relates to a process for the preparation of an improved novel supported bimetallic catalyst which shows activity for hydrogenation of dialkyl esters. This invention particularly relates to preparation of an improved catalysts for the selective conversion of esters of maleic acid to the butyrolactone and tetrahydrofuran. The invention provides a method of preparation of an improved bimetallic supported catalyst, containing one or more transition metals along with a group IV (A) element such as tin, as co-catalyst. Transition metals used are preferably ruthenium or platinum or their mixtures.

2. Description of the Prior Art

In the prior art, metal borides have been studied as catalyst for hydrogenation. Most of these are unsupported boride catalyst. Wade et al have reported preparation and application of copper and cobalt mixed borides in unsupported form in Catal/article Rev Sci Eng 14,211 (1976). They have reported that activity of these borides is sensitive to method of preparation. Indian Patent No. 165540; a research paper in Ind Eng Chem Res 1989, 28, 1110-12 and two publications in J. of catalyst, is report preparation of mixed borides on alumina support. These catalysts are prepared by contacting alumina with mixed solution of salts of ruthenium and tin or ruthenium and germanium. Thus, both metals are impregnated simultaneously. After impregnation catalyst is directly reduced with sodium borohydride. Thus the resulting catalyst exhibits a capacity to convert alkyl esters of dicarboxylic acids to their alcohols along with other bi-products. It is reported that methyl undecenoate, n hexyl acetate and dimethyl succinate are converted to their alcohols along with other products.

DESCRIPTION OF THE INVENTION

The present invention results in a catalyst which shows an activity of hydrogenating dialkyl esters of saturated/unsaturated carboxylic acid to butyrolactone or tetrahydrofuran selectively. The improved process for the preparation of mixed metal boride catalysts essentially consists of using subsequent impregnation of transition metal salt and group IV (A) metal salt, using higher ratios of 1:5 to 1:20 transition metal to tin and using alkali treatment for fixing impregnated metal chlorides. The reduction of metal chlorides and incorporation of boron is done by using sodium borohydride as a reagent. Washing of the catalyst is done by distilled water and finally with alcohol. Accordingly, the first embodiment of the present invention provides a process for the preparation of supported bimetallic catalyst useful for hydrogenation of esters of dicarboxylic acid, which comprises of impregnating activated alumina powder with an aqueous solution of a salt of the transition metal, by contacting the said alumina powder with an aqueous solution of salt of transition metal, treating the said transition metal salt impregnated powder with acidic solution of salt of metals group IV (A) so that the ratio of transition metal to group IV (A) is in the range of 1:5 to 1:20, further treating the bimetallic impregnated alumina powder with an alkali solution followed by a treatment with an aqueous solution of boron containing compound, and finally washing and drying the resultant supported bimetallic catalyst. The transition metals are preferably ruthenium or platinum or their mixtures in chloride form. the group IV (A) metal used may be tin in chloride form in hydrochloric acid. The alkali used may be sodium hydroxide having a normality in the range of 1N to 5N. The impregnation is carried out under stirring for a period of 10 to 20 hrs. The transition metal impregnated on alumina powder ranges, from 0.5% to 2.0%. the ratio of transition metal to group IV (A) metal varies from 1:5 to 1:20.

All percentages and ratios quoted herein are by weight.

The catalyst obtained by the above process surprisingly shows selective hydrogenation of dicarboxylic acid esters. The reason could be that the sequence of steps and chemical reactions adopted in the present process provide such selective hydrogenation property relating to dicarboxylic acid esters. It is well know in the science of catalysts that two catalysts of the same physical and chemical characteristics may have different activities and, therefore, the properties of the catalyst are not sufficient guide in predicting its activity. The other properties which really make the catalyst active are determined by the total history of its preparation.

Prior art processes for liquid phase hydrogenation of carboxylic acid/anhydride/esters using a wide variety of catalysts have been reported in literature. Some of the important vapor phase processes along with their main features are cited below.

A process for the preparation of 1,4 butanediol, butyrolactone and tetrahydrofuran in vapor phase using modified copper chromite catalyst is described in WO patent publication 86/03189. It is a two reaction zone process, operated at 170° C.–190° C. and 190° C.–200° C. respectively. The reactants used are dimethyl maleate and diethyl succinate. Pressures used are of the order of 40 Kg/cm$^2$. Separation of products is affected by condensation of the vapors and subsequent distillation. U.S. Pat. No. 4,268,695 uses copper chromite catalyst but feed to the reactor comprises maleic anhydride and monohydric alcohol. Barium oxide is used as a stabilizing agent for the catalyst. Partial pressure of hydrogen is maintained at 200 bars to 300 bars and temperature of the reaction mixture at 180° C.–300° C. U.S. Pat. No. 4,172,961 describes copper chromite as a catalyst with dibutyldibutoxy succinate as reactant. Main products are 1,4 butatedio and n-butanol with butyrolactone as side product. Selectivity for 1,4 butanediol is reported to be 80%. Reaction conditions employed are 200° C.–300° C. temperatures and pressures upto 4000 psig with 5%–10% catalyst loading. U.S. Pat. Nos. 4,782,167 and 4,550,185 claim a process for preparation of 1,4 butanedio, butyrolactone and THF by hydrogenation of maleic acid/succininc acid in aqueous form with Pd. and Re on titanium dioxide or zirconium di oxide hafnium, dioxide as catalyst. Hydrogenation in a fixed bed reactor at 200° C. and 1000 psig hydrogen pressure gives THF with 51.23% selectivity whereas butyrolactone and 1,4 butanediol are obtained simultaneously with selectivities of 21.66% and 27.11% respectively. Vapour phase processes are run continuously and for economic viability certain plant capacity is required. Vapour phase processes use cheaper conventional catalysts but give multiple products, separation of which is major problem. Also these processes use high ratios of reactant to hydrogen e.g. 1:100 to 1:800, hence hydrogen gas separation and recycle is essential. These are some of the major disadvantages of vapour phase processes. Liquid phase process reported in the lieterature along with their main features are cited below:

Japanese Patent 40-64009 reports Co, Mo, or combination of Co,Mo and Mg as catalyst for hydrogenation of succinic acid. At 200° C. temperature and 300Kg/cm$^2$ pressure, selectivity for 1,4 butanediol is 80%. A combination of Mo, Ni, Ba and Re has been reported as a catalyst in JP Patent No. 63-88045. Hydrogenation of succinic acid at 240° C. and 80 Kg/cm$^2$ pressure gives 80% selectivity for 1,4 butanediol and 5.2% selectivity for THF. JP Patent No. 62-111975 describes the use of a catalyst comprising of Co, Pd, and Ni on NbO or alumina or diatomesecus earth as a catalyst support, with maleic anhydride as the substrate. At 250° C. and 100 Kg/cm$^2$ pressure, a mixture of succinic anhydride, butyrolactone and THF are obtained, with selectivities of 70% and 13.5% for butyrolactone and THF. Copper aluminum borate has been suggested as a catalyst in the U.S. Pat. No. 4,613,70 for hydrogenation of diethyl succinate in an alcohol medium. At 200° C. and 2000 psig pressure, 1,4 butanediol and butyrolactone are obtained as products along with methyl hydroxybutyrate and methyl-4-hydroxybutyl succinate as by-products. A Japanese Patent No. 63 58044 uses a catalyst comprising of metals such as Ni, Mo, Ba and Re. Indian Patent No. 175540 describes a process for the preparation of fatty alcohols by catalytic hydrogenation of carboxylic acids using ruthenium-tin-boride on alumina which has a ratio of ruthenium to tin in the range of 1:1 to 1:1.25. The range of temperatures used is 180° to 70° C. and pressure of 10 to 100 atm. Diethyl succinate on hydrogenation is reported to give 90% conversion with a product containing 80% 1,4 butanediol, 10% THR and 5.5% methanol. Liquid phase processes can be operated as batch or continuous processes. Use of a batch process permits operation with small capacities. Liquid phase processes cited abocve have disadvantages that they have to be operated at very high pressures upto 300 atm and temperatures upto 300° C. None of these processes convert selectively maleic anhydride or its derivatives to butyrolactone and THF. All the processes invariably give 1,4 butanediol besides giving side products such as succinic anhydride hydroxybutyraldehyde and similar products. The separation of these product is a difficult operation. The present invention relates to a process which uses an improved catalyst, to prepare butyrolactone and THF selectively. Side products such as 1,4 butanediol, succinic acid or succinic anhydride are produced in trace quantities. The present invention uses an improved catalyst which gives butyrolactone and THF selectively at milder conditions compared to the prior art.

Accordingly, the second embodiment of the present invention provides an improved process for selective hydrogenation of ester of dicarboxylic acids which comprises hydrogenating an ester of dicarboxylic acid using a novel supported bimelallic catalyst prepared by the process described above, at a temperature in the range of 220° C. to 250° C. and under partial pressure of hydrogen in the range of 1000 psig to 3000 psig for period in the range of 4 hrs to 10 hrs under constant stirring and recovering the product by known methods. The esters of dicarboxylic acid used may be an alkyl ester of maleic acid or succinic acid more preferably diethyl succinate. The bimetallic catalyst used consists of transition metal and group IV (A) metal boride supported on alumina. Preferably it is platinum and tin or ruthenium and tin supported on alumina. The catalyst used may contain platinum or ruthenium upto 2% and ratio of Pt:Sn or Ru:Sn range from 1:5 to 1:20 The amount of catalyst loaded on substrate basis varies from 6% to 75%. The solvents used for dissolving alkyl esters may be selected from ethanol, hexanol, or 1,4 dioxane.

This invention is further illustrated in the following examples which are representative of the process claimed in this invention but these should not be construed to limit the scope of invention in any way.

EXAMPLE 1

10 g of activated alumina powder is contacted with aqueous solution of 0.0929 g PtCl$_3$. This slurry is kept under stirring for 16 hrs. The slurry is dried to obtain a platinum impregnated catalyst. This catalyst is contacted with an aqueous solution of Sn Cl$_2$.2H$_2$O in hydrochloric acid, containing 0.47 g of Sn Cl$_2$.2H$_2$O . Slurry is kept under stirring for 16 hrs, then it is dried. Impregnated catalyst is treated with 5N alkali solution for fixing the metal chlorides. After alkali treatment the catalyst is reduced with 6 times excess of sodium borohydride, by adding the aqueous solution to the suspended catalyst under stirring. Reduced catalyst is filtered, washed with distilled water, and finally with ethanol. this catalyst contains 0.5% platinum and the ratio of Pt:Sn is 1:5.

EXAMPLE 2

A catalyst containing 1.5% platinum was prepared by impregnating 10 g of alumina powder with 0.278 g of Ptcl$_3$ in aqueous form, by stirring the slurry for 16 hrs. The the slurry is dried to get impregnated catalyst. Platinum impregnated catalyst is contacted with 2.82 g of Sncl$_2$2H$_2$O in aqueous form by keeping under stirring for 16 hrs. The slury is filtered dried and treated with aqueous sodium hydroxide (10N) for fixing metal salts. this catalyst is filtered washed and reduced with an aqueous sodium borohydride (0.54 g). Reduced catalyst is filtered washed and dried to get a catalyst containing 1.5% Pt and ratio of Pt:Sn 1:10.

EXAMPLE 3

Catalyst containing 0.5% Pt and Pt:Sn ratio of 1:20 was prepared by contacting 10 g of activated alumina with 0.077 g of PtCl$_3$ solution in water under stirring for 16 hrs. Slurry is dried and further treated with 1.88 g of Sn Cl$_2$.2H$_2$O in hydrochloric acid by stirring for 16 hrs. Impregnated catalyst is filtered and treated with 50 ml of 10N sodium hydroxide. Alkali treated catalyst is filtered washed and treated with 0.5 g of sodium borohydride solution to reduce it. Reduced catalyst is filtered, washed and dried.

EXAMPLE 4

10 g or activated alumina is contacted with 0.1288 g. of Ruthenium chloride trihydrate by stirring for 16 hrs. Slurry is dried and further treated with 0.475 g of acidic solution of Sn Cl$_2$.2H$_2$O by keeping under stirring. Slurry is dried and treated with 10N sodium hydroxide solution to fix metal salt. After fixation of metal salt, catalyst is reduced with 0.319 g of sodium borohydride in aqueous solution. Reduced catalyst is filtered, washed and dried. The catalyst thus prepared has 0.5% of ruthenium and 1:5 ratio of Ru:Sn.

EXAMPLE 5

(Selective hydrogenation of esters of dicarboxylic acids)

In a typical hydrogenolysis experiment 80 ml of diethyl succinate in 1,4 dioxane (17.5 w/w) is charged into a high pressure reactor along with 1 4 g of Pt-Sn-B/Al$_2$O$_3$ catalyst with 0.5% platinum loading and 1:10 ratio of Pt:Sn, reaction vessel is closed and flushed with nitrogen and then subsequently with hydrogen by flushing operations several times. When the temperature is reached agitation is stopped and hydrogen admitted from high pressure reservion to the reactor to a pressure of 2000 psig. Agitation is restarted and reaction is continued for 6 hrs. Hydrogen pressure is made up from a reservoir to maintain pressure at a constant value in the range of 1000 psig to 3000 psig. Similarly the teperature is kept at a constant value in the range of 220° C. to 250° C. Agitation speed is maintained at 800 ppm. After the reaction, product is cooled and analysed by gas chromatographic technique which showed 95% selectivity for butyrolactone at 23.8% conversion. Products are separated by conventional distillation method.

EXAMPLE 6

Reactor is charged with 80 ml of diethyl succinate and 19% of Ru-Sn-BAl$_2$O$_3$ catalyst, with 1% ruthenium and 1:5 ratio of Ru:Sn A reactor is flushed with nitrogen and then with hydrogen pressure is built up to 1300 psig from reservoir. Reaction is carried out at 240° C. for 6.5 hrs under an agitation speed of 800 rpm. Conversion achieved in this period was 48% with 76% selectivity for butyrolactone and 6.6% selectivity for tetrahydroturan.

EXAMPLE 7

A reactor is charged with 80 ml of 17.5% diethyl succinate in n-hexanol. 6 g of catalyst with 1% platinum loading and 1:5 ratio of Pt:Sn. Reaction is carried out at hydrogen pressure of 1000 psig and 240° C. After 6 hrs of reaction under agitation speed of 600 rmp, product is cooled, withdrawn and analysed to show 98% conversion of ester with selectivity of 85% for butyrolactone and 6.6% selectivity for tetrahydrofuran.

EXAMPLE 8

80 ml of 10% diethyl succinate along with 7.5 g of Ru-Sn-B/Al$_2$O$_3$ catalyst containing 1% Ru and 1:5 ratio of Ru:Sn is charged into reactor. A reactor is flushed with nitrogen and then charged with hydrogen to pressure of 1000 psig. A reactor is heated to 220° C. and reaction is carried out for 6 hrs. Conversion of diethyl succinate is 95% with 85% selectivity for butyrolactone.

EXAMPLE 9

100 ml of 10% solution of diethyl succinate in n-hexanol is charged in an autoclave along with 3.7 g of Pt-Sn-B/Al$_3$O$_3$ catalyst containing 1% Ru and 1:5 ratio of Ru:Sn is charged into reactor. A reactor is flushed with nitrogen and then charged with hydrogen to pressure of 1000 psig. A reactor is heated to 250° C. and reaction carried out for 6 hrs. Conversion of diethyl cussinate is 99% with 62% selectivity for butyrolactone and 30% selectivity for THF.

EXAMPLE 10

0.1 moles of diethyl succinate is dissolved in 82.5 g of 1,4 dioxane mixture is charged into reactor with 10% of Pt-Sn-B/Al$_2$O$_3$ catalyst having ratio of Pt:Sn 1:5. A reactor is flushed with nitrogen and then pressurised with hydrogen to 2000 psig. A reaction is carried out at 240° C. to 23.65% conversion and 68% selectivity for butyrolactone with THF as side product.

We claim:

1. A process for the production of butyrolactone or tetrahydrofuran which comprises hydrogenating an alkyl ester of succininc or maleic acid at an elevated temperature in the presence of a bimetallic catalyst obtained by impregnating alumina with an aqueous solution of a salt of a transition metal selected from the group consisting of platinum, ruthenium and mixtures thereof, thereafter treating the impregnated alumina with an aqueous solution of a tin salt so as to have a ratio of transition metal to tin in the range 1:5 to 1:20 and thereafter treating the impregnated alumina with an alkali solution followed by a solution of boron-containing compound.

2. A process as claimed in claim 1 wherein said alkyl ester is diethyl succinate.

3. A process as claimed in claim 1 wherein said boron-containing compound is sodium borhydride.

4. A process as claimed in claim 1 wherein the transition metal comprises 0.5 to 2% of the catalyst.

5. A process as claimed in claim 1 wherein the product is recovered by distillation.

6. A process as claimed in claim 1 wherein the supported bimetallic catalyst contains platinum or ruthenium upto 2% by weight and ratio of Pt:Sn ranges from 1:5 to 1:20.

7. A process as claimed in claim 1 wherein amount of catalyst loaded on substrate varies from 6% to 75% of the weight of substrate.

8. A process for the production of butyrolactone or tetrahydrofuran which comprises hydrogenating an alkyl ester of succinic or maleic acid at a temperature of from 220° C. to 250° C. under partial pressure of hydrogen in the range of 1000 psig to 3000 psig for from 6 to 10 hours under constant stirring in the presence of a bimetallic catalyst obtained by impregnating alumina with an aqueous solution of salt of a transition metal selected from the group consisting of platinum, ruthenium and mixtures thereof, thereafter treating the impregnated alumina with an aqueous solution of a tin salt so as to have a ratio of transition metal to tin in the range 1:5 to 1:20 and thereafter treating the impregnated alumina with an alkali solution followed by a solution of boron-containing compound.

* * * * *